United States Patent
Skinner

[11] Patent Number: 6,022,324
[45] Date of Patent: Feb. 8, 2000

[54] BIOPSY INSTRUMENT

[76] Inventor: Bruce A. J. Skinner, 115 Upton Rd., Sault St. Marie, Canada, P6A 3W2

[21] Appl. No.: 09/002,472

[22] Filed: Jan. 2, 1998

[51] Int. Cl.[7] .................................................. A61B 10/00
[52] U.S. Cl. ......................... 600/566; 600/564; 600/567; 600/583; 606/167
[58] Field of Search .................................. 600/562, 565, 600/566, 567, 568, 573, 583; 606/167, 170, 184, 185

[56] References Cited

U.S. PATENT DOCUMENTS

| | | | |
|---|---|---|---|
| 3,850,158 | 11/1974 | Elias et al. | 128/2 B |
| 4,010,737 | 3/1977 | Vilaghy et al. | 128/2 B |
| 4,461,305 | 7/1984 | Cibley | 600/567 |
| 4,873,991 | 10/1989 | Skinner | 600/567 |
| 4,893,635 | 1/1990 | De Groot et al. | 600/567 |
| 4,903,709 | 2/1990 | Skinner | 600/567 |
| 4,909,249 | 3/1990 | Akkas et al. | 600/567 |
| 5,012,818 | 5/1991 | Joishy | 600/567 |
| 5,019,037 | 5/1991 | Wang et al. | 604/23 |
| 5,040,542 | 8/1991 | Gray | 600/567 |
| 5,060,658 | 10/1991 | Dejter, Jr. et al. | 600/566 |
| 5,146,921 | 9/1992 | Terwilliger et al. | 600/567 |
| 5,234,000 | 8/1993 | Hakky et al. | 600/567 |
| 5,257,632 | 11/1993 | Turkel et al. | 600/567 |
| 5,507,298 | 4/1996 | Schramm et al. | 600/567 |
| 5,511,556 | 4/1996 | DeSantis | 600/567 |
| 5,560,373 | 10/1996 | De Santis | 600/566 |
| 5,769,086 | 6/1998 | Ritchart et al. | 600/566 |
| 5,817,033 | 10/1998 | DeSantis et al. | 600/564 |

FOREIGN PATENT DOCUMENTS

| | | | |
|---|---|---|---|
| 1118655 | 2/1982 | Canada | 128/82 |
| 1222669 | 6/1987 | Canada | 128/2 |
| 2071212 | 6/1991 | Canada | |
| 2059875 | 8/1992 | Canada | |

*Primary Examiner*—Cary O'Connor
*Assistant Examiner*—Charles Marmor, II
*Attorney, Agent, or Firm*—Michael Best & Friedrich LLP

[57] ABSTRACT

A biopsy instrument which can be used to take a bone biopsy sample or a soft tissue biopsy sample. The biopsy instrument includes a biopsy needle and a biopsy gun. The biopsy gun includes a firing mechanism for firing the biopsy needle with a minimum force for striking and penetrating the target tissue organ; a cradle that securely holds the biopsy needle with an attached disposable syringe having a plunger; and a triggering mechanism. In operation, the triggering mechanism actuates the firing mechanism causing the cradle together with the needle and the attached syringe to fire forward with a sufficient force such that the needle penetrates the target tissue organ causing a first a first tissue sample to be cored in the needle. The disposable syringe can then be used to obtain a second tissue sample up through the biopsy needle using a vacuum created in the disposable syringe when the plunger is maintained in a rearward position while the syringe fires forward. In a bone biopsy procedure, the first tissue sample is a bone sample and the second tissue sample is a liquid bone marrow sample.

13 Claims, 4 Drawing Sheets

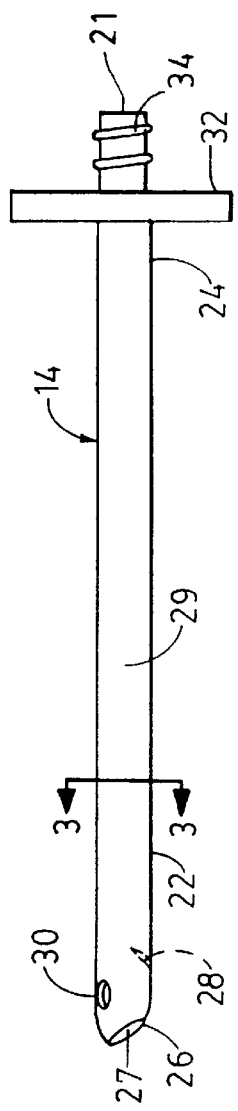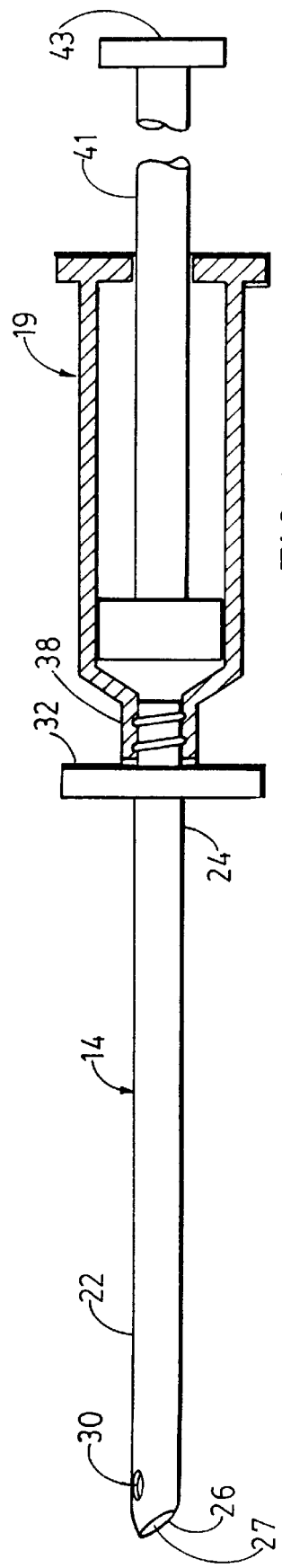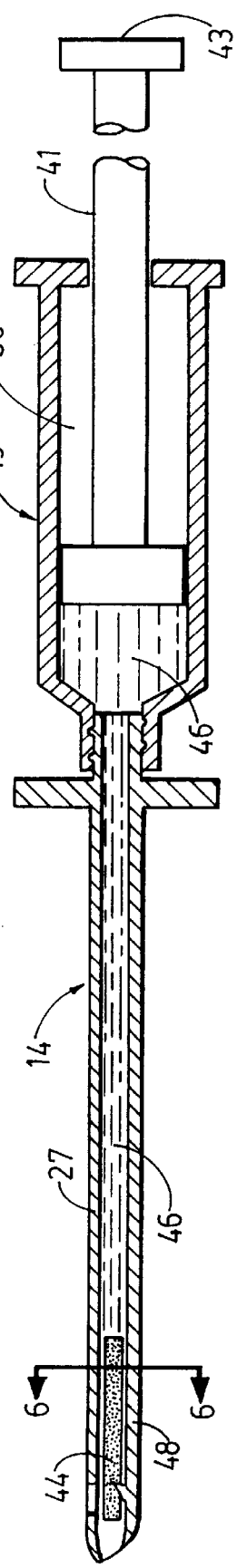

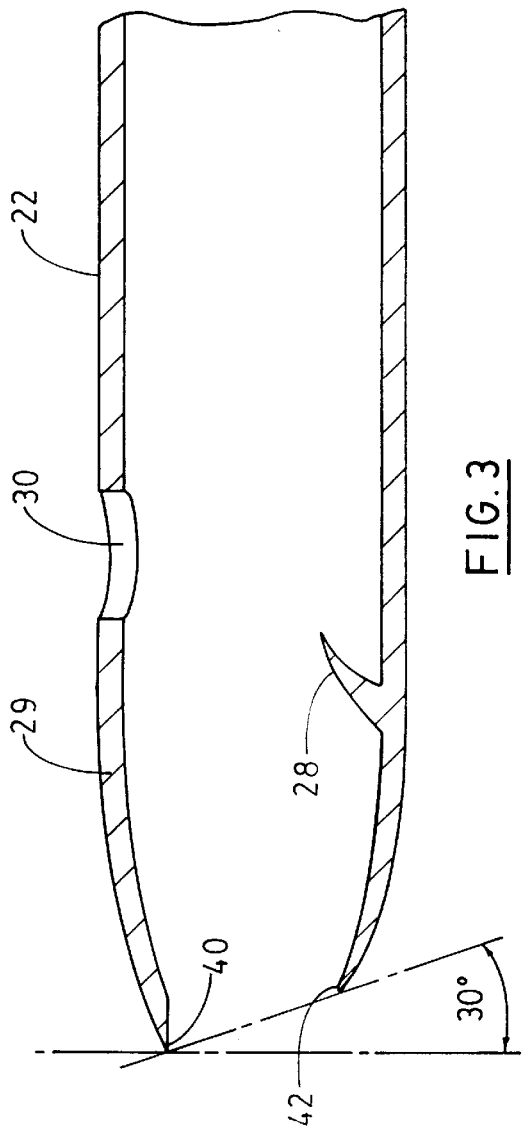
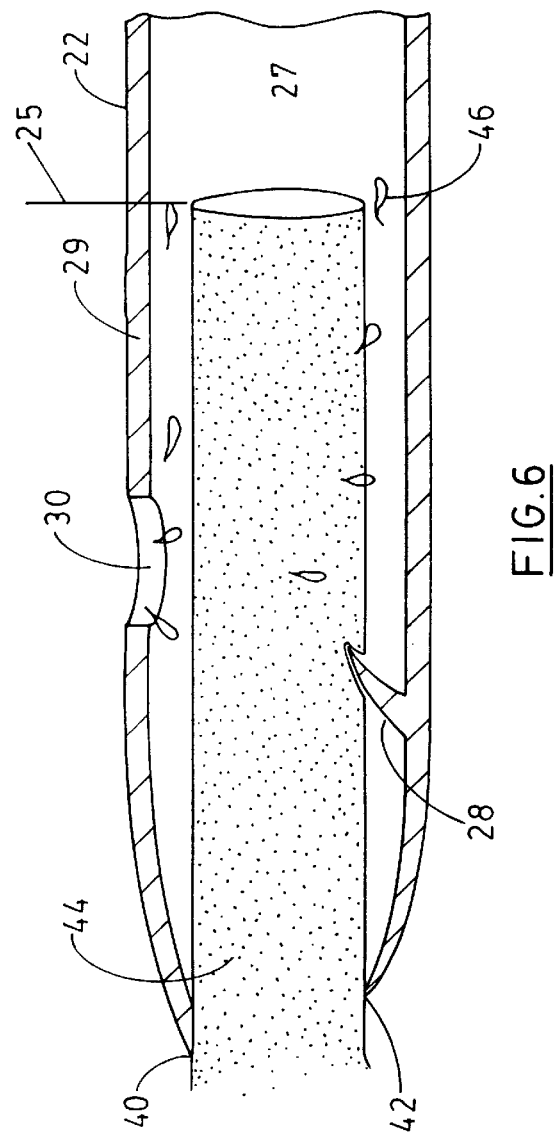

BIOPSY INSTRUMENT

FIELD OF THE INVENTION

The present invention is directed to a biopsy instrument. In particular, the present invention is directed to a biopsy instrument comprising a biopsy gun and a biopsy needle.

BACKGROUND

Biopsy instruments of the prior art are generally biopsy needles which are sued by hand or biopsy guns which together with biopsy needles are used to obtain samples. The biopsy needles of the prior art have been directed to bone biopsy needles and to soft tissue biopsy needles. The biopsy guns of the prior art have been directed to soft tissue biopsy guns.

Bone biopsy needles have generally been cumbersome and very difficult instruments to use. As a result, bone biopsy procedures using bone biopsy needles are generally painful and traumatic procedures. The doctor manually inserts a needle through the skin into the bone and because the bone is hard the needle is very difficult to insert. It requires a lot of strength to push the needle into the bone. Once the needle is inserted into the bone, the needle is manipulated in an attempt to break off a piece of bone in the needle and then a syringe is placed on the end of the needle to aspirate the liquid bone marrow up into the needle. Unfortunately, often the liquid bone marrow can not properly be retained in the needle because the bone sample in the needle is blocking the entrance into the needle and thereby blocking the passageway for the liquid bone marrow. Furthermore, the bone sample is difficult to maintain in the needle. As a result, bone biopsies using such needles are not only painful and traumatic but are quite often not completed properly since the liquid bone marrow sample and the cored solid bone sample are not properly retained in the needle.

The Jamshidi needle of the prior art is used for obtaining bone biopsies and is the current standard means for obtaining such biopsies. The needle comprises a hollow tube, one end of which is swaged to taper the end. As the tapered end penetrates the bone marrow, a core of the tissue passes into the lumen of the needle and the tapered end is manipulated to cut off the cored bone. This needle does not provide an adequate mechanism for removing the liquid bone marrow since the opening on the needle is effectively plugged by the cored bone.

Most of the soft tissue biopsy needles of the prior art are generally known as tru-cut type needles. Tru-cut needles have a gutter drilled out of one end of the needle and a cannula or sleeve which slides over the gutter. After the tru-cut needle is inserted into the soft tissue, the soft tissue falls into the gutter and the cannula is then pushed forward over the gutter slicing the tissue off into the gutter. As the true-cut needle is withdrawn, the tissue is maintained in the gutter.

There are also other types of soft tissue biopsy needles, such as the soft tissue biopsy needle described in U.S. Pat. No. 4,903,709 to Skinner. Skinner describes a soft tissue needle in which there is a lanced portion formed from the sidewall of the needle which lanced portion assists in slicing the soft tissue.

The soft tissue needles of the prior art are not suitable for bone biopsies. The soft tissue needles are not strong enough to withstand the force on the needle necessary to penetrate the bone. Furthermore, with respect to the tru-cut needles, the bone tissue is too hard and as such it does not fall into the gutter of the needle and therefore is not appropriate for bone biopsies. With respect to the biopsy needle described in Skinner, it is not suitable for bone biopsies as there is no means for obtaining a liquid bone marrow sample in the needle. A proper bone biopsy requires a sample of the liquid bone marrow as well as a sample of the solid bone.

There are many biopsy guns of the prior art which are used together with a biopsy needle. The biopsy guns of the prior art are designed to be used to biopsy soft tissues often with a tru-cut needle and are not suitable for bone biopsies, as described above. The biopsy gun fires the tru-cut needle into the larger soft tissue and as the needle penetrates the soft tissue the soft tissue falls into the gutter. The biopsy gun then fires a metal sheath or cannula on the needle over the gutter slicing the soft tissue off into the gutter.

U.S. Pat. No. 5,146,921 to Terwilleger et al. describes a biopsy instrument for removing soft tissue sample. The soft tissue penetrating needle has an inner stylet and a cannula. The inner stylet penetrates the soft tissue mass. The inner stylet is notched so that when the stylet penetrates the soft tissue a portion of the soft tissue falls into the notched area. The cannula then slides over the stylet severing the soft tissue in the notched area. Both the penetration of the inner stylet into the soft tissue and the severance of this soft tissue by the cannula are actuated by actuating a fire button. A second button, a retraction button, can then be depressed to retract the canula. Then the second button is retracted a second time to retract the stylet from the soft tissue. The actuation of the stylet and cannula is possible by the rotary motion of a special cam assembly. There are essentially three positions of the bone biopsy gun; where both stylet and cannula are forward; where the stylet is forward and the cannula is retracted; and where both the stylet and cannula are retracted. This biopsy instrument is not suitable for bone biopsies since, among other things, the bone tissue could not be collected using the needle described.

U.S. Pat. No. 5,234,000 describes an automatic biopsy device housing a plurality of stylets to permit multiple soft tissue biopsy samples to be taken. The stylets are used in conjunction with a cannula. The device is operated by an actuating trigger means which propels the stylet through the cannula into the target organ so that a portion of the soft tissue enters a recess of the selected stylet and then the cannula is propelled over the stylet slicing the soft tissue into the recess. When the trigger is released the stylet and cannula retract out of the target organ.

U.S. Pat. No. 4,461,305 describes an automated biopsy device for automatically extracting soft tissue samples, particularly from the uterine cervix. The device has a core-cutter which is advanced into the target tissue to a certain depth cutting away the soft tissue as it penetrates the soft tissue by depressing an actuated trigger. When the trigger is released the rotation of the core cutter ceases. A reset knob is then manually rotated by the operator to return the core-cutter to the original position.

As discussed above, the biopsy instruments and needles of the prior art which are used for obtaining soft tissue samples are not suitable for bone biopsies. A bone sample, including a liquid bone marrow sample, can not be properly obtained with these prior art instruments and needles. In particular, with respect to the stylet and cannula assemblies of the prior art, the bone sample would not fall into the notched area in the stylet and therefore a bone sample could not be obtained. In addition, these instruments have not been designed to withstand the forces exerted on the needle during a bone biopsy in contrast to a soft tissue biopsy.

It is desirable to have a biopsy instrument which is designed so that it has enough force to effectively sample bone tissue. It is also desirable to have a biopsy instrument which is hand held and is designed so that a bone sample may be taken requiring very little, if any, manual strength. Furthermore, it is desirable to have a biopsy instrument which can be used to obtain a bone sample and a liquid bone marrow sample in a single biopsy procedure. It is also desirable to have a biopsy instrument that makes the biopsy process less traumatic and painful, requires less time to conduct and requires less operator expertise and therefore is more reliable, reducing multiple procedures.

A proper bone biopsy requires both a bone sample and a liquid bone marrow sample. The procedure as practised suing the prior art bone biopsy needles is painful and requires an operator's strength and skill. Often, multiple attempts are necessary to obtain a proper bone marrow biopsy. Furthermore, for bone marrow disease it is often desirable to take bone biopsies successively and repeatedly at different intervals to monitor the progress or regression of the disease increasing the anxiety of the patient in view of the pain caused by the procedure. Accordingly, it is desirable to provide a more reliable biopsy instrument, requiring less operator expertise, reducing the likelihood of multiple attempts and reducing the time required to take a biopsy sample.

It is also desirable to have a biopsy instrument comprising a biopsy gun and a biopsy needle which can be used to obtain a bone sample and a liquid bone marrow sample in a single bone biopsy procedure or which can be used to obtain a soft tissue sample in a single soft tissue biopsy procedure.

SUMMARY OF INVENTION

According to an aspect of the present invention there is provided a biopsy instrument which can be used to take a bone biopsy sample or a soft tissue biopsy sample.

According to another aspect of the present invention there is provided a biopsy instrument comprising a biopsy gun and a biopsy needle which effectively takes a first and second tissue sample in one biopsy procedure and which requires very little manual strength. For bone biopsy procedures, the biopsy gun is powered by an energy source such that it provides the needle with a force sufficient to penetrate the bone. It has been observed that in some cases 200 pounds of force has been a sufficient amount of force to cause the needle to penetrate the bone.

According to an aspect of the invention there is provided a biopsy instrument for obtaining a tissue sample from a target soft tissue organ or a target bone organ, and the biopsy instrument comprising a biopsy needle and a biopsy gun, the biopsy gun comprising a firing mechanism for firing the biopsy needle with a minimum force for striking and penetrating the target tissue organ, a cradle, wherein the cradle securely holds the biopsy needle with an attached disposable syringe having a plunger, and a triggering mechanism such that the triggering mechanism, when actuated, actuates the firing mechanism causing the cradle together with the needle and attached syringe to fire forward with a sufficient force such that the needle penetrates the target tissue organ causing a first tissue sample to be cored in said needle. The disposable syringe can then be used to obtain a second tissue sample up through the biopsy needle using a vacuum created in the disposable syringe when the plunger is maintained in a rearward position while the syringe is fired forwards. In a bone biopsy procedure, the first tissue sample is a bone sample and the second tissue sample is the liquid bone marrow sample.

According to a further aspect of the invention there is provided a biopsy instrument for obtaining a tissue sample from a target tissue organ comprising a biopsy needle and a biopsy gun wherein the biopsy gun further comprises a firing mechanism in which the cradle is fired forwards in a forward stroke after said triggering mechanism is depressed and is then automatically retracted backwards after a predetermined time interval.

According to another aspect of the present invention there is provided a biopsy instrument further comprising an outer housing in which the biopsy needle sits and in which the biopsy needle travels. In a preferred embodiment, the outer housing provides a guide for positioning the needle to the target tissue organ. Preferably, the biopsy needle is retracted inside the outer housing prior to firing the biopsy needle at a position such that when the biopsy needle is fired forwards and strikes the target tissue organ it has reached a desired velocity for penetrating the target tissue organ.

According to another aspect of the present invention there is provided a biopsy instrument comprising a biopsy gun and a biopsy needle wherein the biopsy needle comprises a tubular wall defining a lumen, a proximal end and a distal end wherein the proximal end has a first opening defined by one end of the tubular wall and said proximal end has one or more second openings in the side of the tubular wall of the needle. As described herein, the proximal end is closer to the target tissue organ and, accordingly, the distal end is further from the target tissue organ and closer to the operator.

According to another aspect of the present invention there is provided a biopsy instrument comprising a biopsy gun and a biopsy needle wherein the biopsy needle is designed to take a first tissue sample in part of the needle lumen and a second tissue sample in another part of the needle lumen. The first tissue sample is a cored bone sample and the second tissue sample is a liquid bone marrow sample when the biopsy instrument is used to take a bone biopsy.

According to another aspect of the present invention, there is provided a biopsy instrument comprising a biopsy gun and a biopsy needle, the biopsy needle having a proximal end and a distal end, the proximal end having a first opening for receiving a first tissue sample and one or more second openings for receiving a second tissue sample. The first tissue sample is a cored bone sample and the second tissue sample is a liquid bone marrow sample when the biopsy instrument is used to take a bone biopsy.

According to another aspect of the present invention there is provided a biopsy needle wherein the biopsy needle comprises a tubular wall defining a lumen, a proximal end and a distal end wherein the proximal end has a first opening defined by the end of the tubular wall which is swaged or tapered at said opening and one or more second openings in the side of said tubular wall so that when a cored bone sample is taken up through the first opening the cored bone sample occupies the central portion of the lumen and the liquid bone marrow sample is then taken up through the one or more second opening and occupies the circumferential part of the lumen not occupied by the cored solid bone sample.

According to another aspect of the present invention there is provided a biopsy gun to be used together with a biopsy needle for obtaining a bone biopsy sample or a soft tissue biopsy sample which when actuated caused the needle to penetrate into the tissue without the operator having to use his/her manual strength. When the bone is biopsied, the bone is cored into the lumen of the needle through a first opening and the liquid bone marrow is then aspirated through one or more second opening in the tubular wall of the needle into the lumen unoccupied by the bone sample by an attached syringe. When the biopsy gun fires the needle with attached syringe forwards obtaining a solid bone sample a vacuum is created in the syringe and the biopsy needle. The liquid bone marrow is then taken up through the biopsy needle and into the syringe due to the vacuum pressure. The needle is then withdrawn from the bone.

According to a further aspect of the invention there is provided a hand held operated re-usable biopsy gun to be used with a biopsy needle to obtain a tissue sample from a target tissue organ, the biopsy gum comprising a firing mechanism for firing the biopsy needle with at least a force great enough for striking and penetrating the target tissue organ a triggering mechanism a cradle for holding a biopsy needle and a disposable syringe, said disposable syringe is attached to the biopsy needle and the disposable syringe comprising a plunger, such that on the actuation of the triggering mechanism, the firing mechanism is actuated causing the cradle together with the biopsy needle to move forward in a forward stroke striking the target tissue organ causing a first tissue sample to be cored off into the needle and the syringe is then used to obtain a second tissue sample using a vacuum created when the plunger is maintained in a rearward position while the syringe is fired forwards.

BRIEF DESCRIPTION OF THE DRAWINGS

The following drawings are illustrations of particular embodiments of the bone biopsy instrument comprising the biopsy gun and the biopsy needle of the present invention and in no wary are intended to restrict the scope of the present invention.

FIG. 2 is an illustration of a side view of an embodiment of the biopsy needle of the present invention.

FIG. 3 is an illustration of a cross-sectional view along longitudinal line 3—3 of the embodiment of the biopsy needle of the present invention of FIG. 2.

FIG. 4 is an illustration of a side view of a biopsy needle of the present invention of FIG. 2 with a syringe attached thereto.

FIG. 5 is an illustration of a cross-sectional view of the withdrawal of a bone sample and liquid bone marrow sample with attached syringe of FIG. 4.

FIG. 6 is an illustration of a cross-sectional view along longitudinal line 6—6 of FIG. 5 illustrating the withdrawal of a bone sample and liquid bone marrow sample.

DETAILED DESCRIPTION

Figure 1:
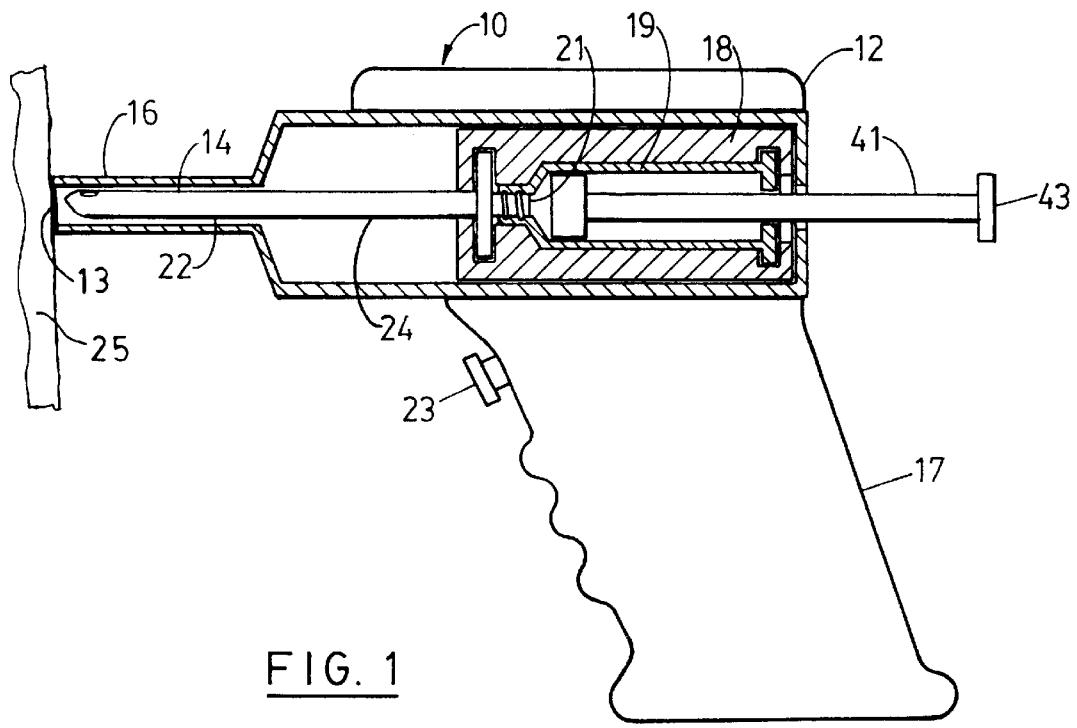
FIG. 1 is an illustration of a longitudinal partial cross sectional view of an embodiment of the biopsy instrument of the present invention.

Referring to FIG. 1, an embodiment of the biopsy instrument of the present invention is shown at 10. The biopsy instrument 10 comprises the biopsy gun 12 and the biopsy needle 14. The biopsy instrument 10 has an outer housing 16 at the forward end in which the proximal end 22 of the biopsy needle 14 sits. The biopsy gun has a hand held portion 17 in which the firing mechanism is situated.

The distal end 24 of the needle 14 sits within a cradle 18 in the bone biopsy gun 12. In the cradle 18 is a syringe 19 which is attached to the distal tubular opening 21 of the distal end 24 of the biopsy needle 14. Syringe 19 has a plunger 41 with a handle 43. Handle 43 is locked in position so that it does not travel forwards when the biopsy needle 14 is fired into the target organ 25.

The cradle 18 and in particular the biopsy needle 14 together with the syringe 19 must be accessible so that the samples can be retrieved from the needle 14 and the syringe 19 for testing.

The biopsy gun 12 has a trigger button 23 on the hand held portion 17 of the biopsy gun 12. The trigger button 23 when actuated causes the firing mechanism in the biopsy gun 12 to fire the cradle 18 with the needle 14 and the attached syringe 19 forward so that the needle 14 exist the outer housing 16 and punctures the target organ 25 of the subject. Prior to firing, the outer housing 16 allows the operator to align the needle 14 with the area on the target organ 25 in which a sample is desired.

The biopsy needle 14 is illustrated in FIGS. 2 to 4. In FIGS. 5 and 6 the biopsy needle is illustrated taking a bone biopsy. The biopsy needle 14 when used to take a bone biopsy is generally about 10 cm in length and generally about 0.5 cm in diameter. However, the dimensions may change depending on the subject and the target tissue being sampled.

The biopsy needle 14 is generally a hollow tubular shape with tubular wall 29 defining a lumen 27 inside said needle 14 and a proximal end 22 and a distal end 24, wherein said proximal end is closer to said target organ 25 then said distal end.

At the proximal end 22 of the biopsy needle 14 there is an opening 26 through which the sample is taken. The tubular wall 29 at proximal end 26 tapers inwards towards the opening 26. On one side of the tubular wall 29 of the biopsy needle 14 at the proximal end 22 there is a triangular flap 28 and a second opening 30. Triangular flap 28 and second opening 30 may be in the same horizontal plane of the tubular wall 29 or different horizontal planes as illustrated in FIG. 2. Triangular flap 28 assists in breaking off a first tissue sample within the lumen 27 of the biopsy needle 14 and the second opening 30 is used to aspirate a second tissue sample. The second tissue sample may in certain circumstances simply be a number of cells in a liquid. In particular, as illustrated, when a bone biopsy procedure is being conducted, the triangular flap 28 assists in breaking off the cored bone and the second opening 30 is used to aspirate the liquid bone marrow fluid into the part of lumen 27 of the bone biopsy needle not occupied by the cored bone sample.

At the distal end 24 there is a large metal flange 32 and a threaded fastener 34 with a distal tubular opening 21. The large metal flange 32 provides the necessary support to the needle to absorb the force which is exerted on the biopsy needle 14 when it is being inserted into a target bone organ.

Referring to FIGS. 2 and 3, the proximal end 22 and tubular wall 29 are shown. The tubular wall 29 of the biopsy needle 14 is thick enough to withstand the necessary force required to insert the needle 14 into the target organ taking into account the force absorbed by the large metal flange 32. The tubular wall 29 tapers inwards towards opening 26. Tubular wall 29 at opening 26 is slanted so that one side 40 of the end of tubular wall 29 extends forward over an opposing side 42 of tubular wall 29. In a preferred embodiment of the needle 14, tubular wall 29 is slanted at one side 40 such that it extends forward at an angle of approximately 30 degrees with the transverse axis of the needle, as shown in FIG. 3.

Referring to bone biopsies, as illustrated in FIGS. 5 and 6, tubular wall 29 of the needle 14 is tapered at one part 40 to a relatively sharp point to facilitate the insertion of the needle 14 through the tissue and the bone. Side 40 of tubular wall 29 together with the slanted opening at the proximal end 22 provide a sharp means for cutting into the bone sample 44. Triangular flap 28 grasps the bone sample 44 causing the bone sample 44 to separate from the target bone organ 25 as the needle 14 is withdrawn from the target bone organ 25. Triangular flap 28 also assists in maintaining the bone sample 44 in the lumen 27 of the needle 14 after the needle 14 is withdrawn.

The biopsy needle 14 is attached to a syringe 19 by attaching the forward end 38 of the syringe 19 to the threaded fastener 34 of the biopsy needle 14. Syringe 19 has a plunger 41 and handle 43.

When the biopsy needle 14 is inserted into a subject, the proximal end 22 of the needle 14 pierces the target bone 25. If enough force is applied, the insertion of the needle 14 into the bone will core bone sample 44 within lumen 27. A vacuum is then created in syringe 19 for aspirating the liquid bone marrow through the second opening 30 into the lumen 27 of the biopsy needle not occupied by the bone sample 44 and thereby obtaining a liquid bone marrow sample 46 by aspirating the liquid bone marrow through the second opening 30.

The opening 26 is smaller in diameter than the diameter of the lumen 27 in needle 14 so that when the bone sample 44 is taken up into the lumen 27 of the biopsy needle 14 there is an area surrounding the bone sample 44 which is empty and permits an unobstructed space 48 up around the circumference of the lumen 27 in which to aspirate the liquid bone marrow sample 46 up into the lumen 27 through second opening 30 and into the vacuum chamber 50 of syringe 19 created when the syringe 41 is fired forwards while the plunger 41 is in a withdrawn position at the rear portion of the syringe 19. In addition, the bone sample 44 tends to obstruct opening 26 to help prevent the liquid bone marrow 44 from leaking out opening 26.

Referring to FIG. 6, triangular flap 28 is shown piercing into the bone sample 44 such that the bone sample 44 is held in place in the lumen 27 of the needle 14.

Triangular flap 28 preferably extends approximately ⅓ of the way into the diameter of the lumen 27 of the biopsy needle 14. When the triangular flap 28 extends approximately ⅓ of the way into the diameter of the lumen 27 it provides an appropriate amount of leverage on the bone sample 44 assisting in severing the bone sample 44 from the target bone organ 25 and preventing the bone sample 44 from sliding out the opening 26 while the biopsy needle 14 is withdrawn from the subject.

The biopsy needle 14 and biopsy gun are preferably made out of stainless steel and are of a suitable gauge to withstand repeated use. Stainless steel permits the biopsy needle 14 and biopsy gun 12 to be sterilized and re-used. However, other materials or metals could be used, such as titanium. However, in some circumstances, it may be desirable to have a disposable biopsy needle 14 in which case other materials may be used to construct the biopsy needle 14. The materials of the biopsy needle 14 must be able to withstand the force exerted on it.

The second opening 30 can be just one opening or hole as shown in the figures or there can be more than one opening for aspirating a sample, or in particular with respect to bone biopsies for aspirating a liquid bone marrow sample.

Figure 7:
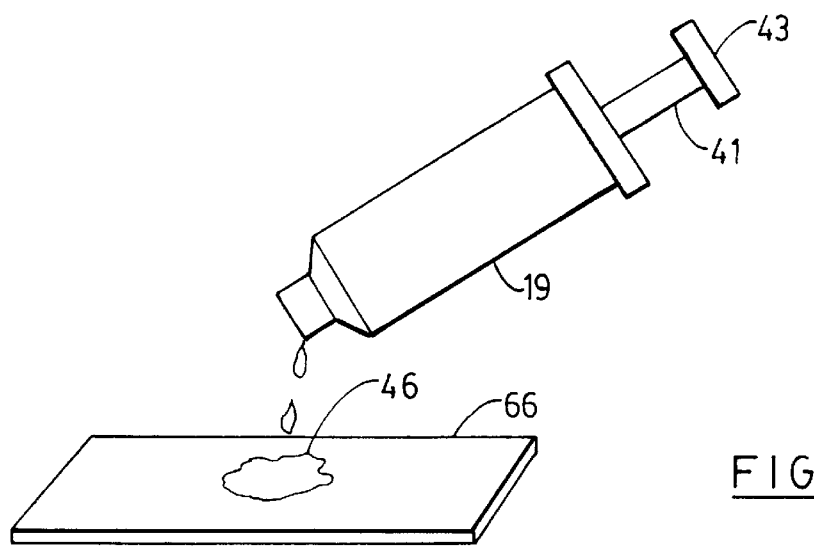
FIG. 7 is an illustration of the removal of the liquid bone marrow sample taken from the syringe attached to the biopsy needle.
Figure 8:
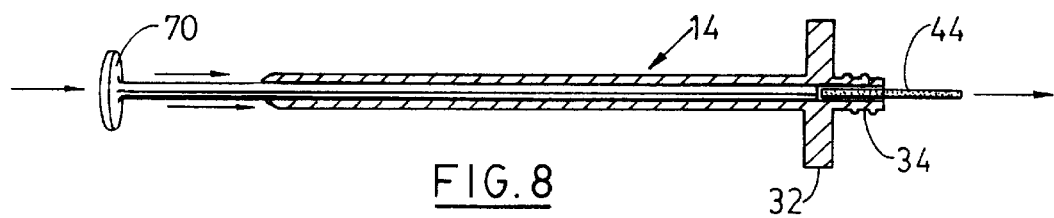
FIG. 8 is an illustration of the removal of the bone sample from the biopsy needle.

Referring to FIGS. 7 and 8, after the biopsy needle 14 is withdrawn from the subject, the syringe is taken off the biopsy needle 14 and the liquid bone marrow sample 46 can be tested by placing it onto glass slides 66 for staining/fixing for microscopic examination. Bone sample 44 can be removed from needle 14 using a metal rod 70 which is inserted through opening 26 of the needle 14 to push the bone sample 44 through the distal end 28. The triangular flap 28 is such that the bone sample must be taken out through the distal end 28 and can not easily be taken out the proximal end 22 of the biopsy needle 14.

Figure 9:
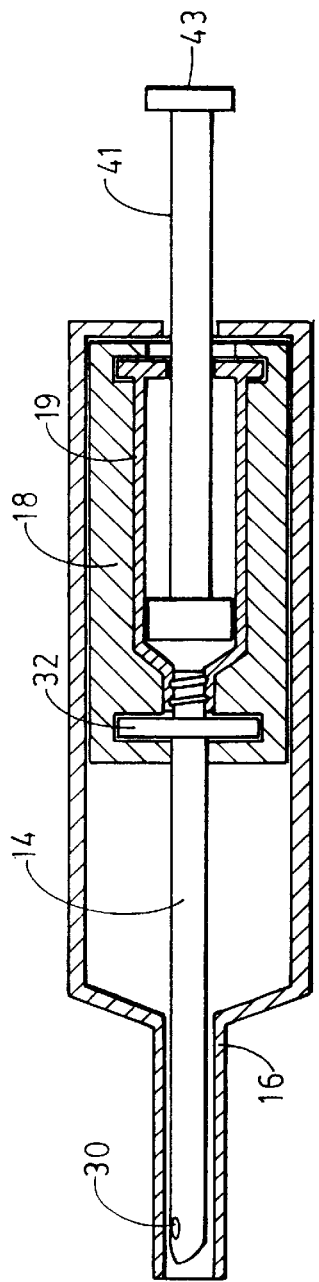
FIG. 9 is an illustration of a longitudinal partial cross section of the biopsy needle and attached syringe in the cradle of the biopsy instrument of the present invention prior to firing the biopsy needle.
Figure 10:
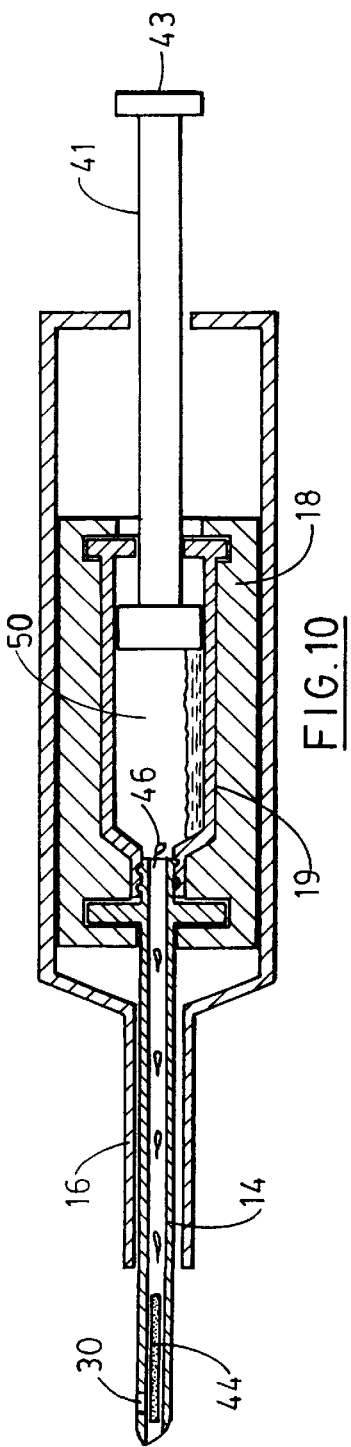
FIG. 10 is an illustration of a partial longitudinal cross section of the biopsy needle and attached syringe in the cradle of the biopsy instrument of the present invention at the end of the forward stroke of the biopsy needle.
Figure 11:
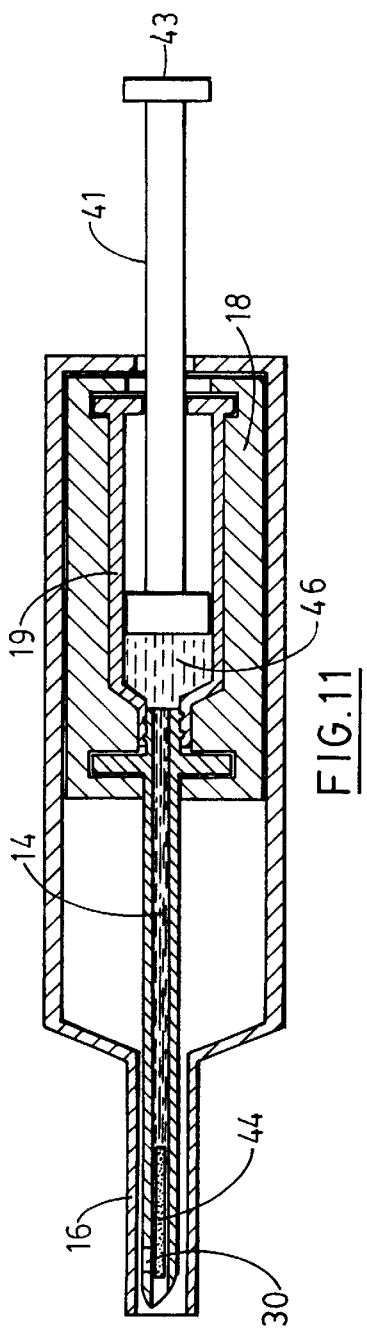
FIG. 11 is an illustration of a partial longitudinal cross section of the biopsy needle and attached syringe in the cradle of the biopsy instrument of the present invention at the end of the backward stroke of the biopsy needle.

Referring to FIGS. 9, 10, and 11, the biopsy instrument 10 is illustrated taking a bone biopsy sample as follows: prior to the biopsy needle 14 being fired by the biopsy gun 12; after the biopsy needle 14 is fired by the biopsy gun 12 when the biopsy needle 14 is in the forward stroke position; and on return of the biopsy needle 14 backwards from the forward stroke, respectively. Referring to FIG. 9, prior to depressing the trigger button 23; the cradle 18 is positioned in a retracted position with the biopsy needle 14 withdrawn into the outer housing 16. When the trigger button 23 is depressed, referring to FIGS. 10 and 11, it actuates the firing mechanism in the hand portion 17 of the biopsy gun 12 causing the cradle 18 together with the biopsy needle 14 and attached syringe 19 to be fired forward in a forward stroke. The biopsy needle 14 extends forward into the outer housing 16 and out the exit 13 puncturing the bone in the forward stroke. The biopsy needle 14 strikes the bone at a force which is sufficient to obtain a cored bone sample in the biopsy needle 14. When the cradle 18 together with the biopsy needle 14 and attached syringe 19 is fired forwards, the handle 43 of the plunger 41 of the syringe 19 is maintained in a rearward position creating a vacuum in the syringe 19 as syringe 19 fires forwards while the plunger 41 is maintained in the rearward position. The vacuum in the syringe 19 causes the liquid bone marrow to enter the second opening 30 and be drawn into lumen 27 of the biopsy needle 14 and up into the cavity of syringe 19.

After the cores solid bone sample and liquid bone marrow sample are obtained, the cradle 18 retracts backwards from the forward stroke in the biopsy gun 12 causing the biopsy needle 14 to retract backwards in the outer housing 16 withdrawing the biopsy needle 14 from the bone. The cored bone sample 44 is severed and maintained in the needle by the triangular flap 28. Once the biopsy needle 14 is fully retracted the biopsy needle 14 together with the syringe 19 is removed from the biopsy gun 12. The cored bone sample 44 and the liquid bone marrow sample 46 can then be tested, as described above.

The firing mechanism is preferably operated on a timer so that there is minimal judgement required by the operator. Thereby, by one depression of the trigger button 23 it causes the biopsy needle 14 to move forward in the forward stroke and after a certain time period the biopsy needle 14 is automatically retracted backwards into the outer housing 16. In a preferred embodiment the biopsy needle is automatically retracted after approximately 0 to 3 seconds. In a further preferred embodiment the time period after the biopsy needle 14 is fired forwards and before the biopsy needle 14 is retracted is manually adjustable.

Other alternatives of the firing mechanism are possible. The firing mechanism could be designed so that the forward stroke occurred after a first depression of a trigger mechanism and the backward stroke occurred after a second depression of a trigger mechanism.

In a preferred embodiment, the biopsy instrument has means for adjusting the length of the biopsy needle's penetration into the target organ depending on the subject, the desired sample and the target organ.

The syringe used is preferably a standard disposable lab syringe. The syringe must create a tight fit at the distal opening 21 on the threaded fastener 34 of the biopsy needle 14 so that it will create a vacuum when the syringe is fired forwards and the plunger 41 is maintained in a rearward position. Any type of fastener may be used which will create a tight seal with the syringe and allow a vacuum to be created when the plunger 41 is withdrawn The firing mechanism of the biopsy instrument of the present invention may take a number of forms. Preferably, the firing mechanism will: provide a sufficient force so that it will penetrate the target tissue organ quickly with little pain; be light weight; and be small enough that it can be incorporated into a biopsy gun which can be held in the hand of the operator. In a preferred embodiment, the firing mechanism comprises a small motor which is battery operated wherein the battery is a rechargeable battery. In which case, the biopsy instrument can be stored in a battery charger in between biopsy procedures. Other suitable firing mechanisms would be known by persons skilled in the art and could include gas cylinder powered mechanisms and electrically powered mechanisms.

It is to be understood that the above embodiments are illustrations of the invention and may be modified without departing from the scope of the invention as claimed.

I claim:

1. A biopsy instrument for obtaining a tissue sample from a target organ, said target organ being a soft tissue organ or a bone organ, said biopsy instrument comprising:
   a biopsy needle; and
   a biopsy gun having a firing mechanism for firing said biopsy needle with a minimum force for striking and penetrating said target tissue organ, a cradle securely holding said biopsy needle and an attached disposable syringe, said disposable syringe comprising a housing and a plunger, and a triggering mechanism that when actuated, actuates said firing mechanism causing said cradle with said needle and attached syringe to fire forward with a sufficient force for penetrating the target tissue organ, a first tissue sample being cored in said needle and said disposable syringe being used to obtain a second tissue sample up through said biopsy needle using a vacuum created in said disposable syringe when said plunger is maintained in a rearward position while said syringe is fired forwards.

2. A biopsy instrument according to claim 1, wherein said tissue sample is a soft tissue sample, said target tissue organ is a soft tissue organ, and said first and said second tissue samples are soft tissue samples.

3. A biopsy instrument according to claim 1, wherein said tissue sample is a bone sample, said target tissue organ is a target bone organ, said first tissue sample is a solid bone sample, and said second tissue sample is a liquid bone marrow sample.

4. A biopsy instrument according to claim 1, wherein said biopsy gun further includes a firing mechanism in which the cradle is fired forward in a forward stroke after said triggering mechanism is depressed and is then automatically retracted backwards after a predetermined time interval.

5. A biopsy instrument according to claim 4, wherein said specific time interval is approximately 0–3 seconds to permit a liquid bone marrow sample to be obtained when said biopsy instrument is used to obtain a bone sample from a target bone organ.

6. A biopsy instrument according to claim 1, wherein said biopsy instrument has an outer housing in which said biopsy needle sits and in which said needle travels, said needle retracted in said outer housing prior to firing said biopsy needle such that said outer housing provides a guide for positioning said biopsy needle to said target organ and wherein said biopsy needle is retracted in said outer housing at a position which permits said biopsy needle to reach a desired velocity when said biopsy needle is fired forwards and strikes said target organ.

7. A biopsy instrument according to claim 1, wherein said biopsy needle includes a tubular wall defining a lumen, a proximal end and a distal end wherein said proximal end has a first opening and said tubular wall at said proximal end is tapered inwards towards said opening defining said opening and wherein said proximal end has one or more second openings in said tubular wall, wherein said first opening is used to obtain said first tissue sample and said one or more second openings in said tubular wall of the biopsy needle is used to obtain said second tissue sample wherein the diameter of the first opening at said proximal end of said biopsy needle is less then the diameter in said lumen.

8. A biopsy instrument according to claim 7, wherein said tissue sample is a bone sample, said target tissue organ is a target bone organ, said first tissue sample is a solid bone sample, and said second tissue sample is a liquid bone marrow sample.

9. A biopsy instrument according to claim 8, wherein said first tissue sample is a cored bone sample and said second tissue sample is a liquid bone marrow sample.

10. A biopsy instrument according to claim 7, wherein said first opening is defined by said tubular wall and said tubular wall is slanted at said first opening to facilitate insertion of the needle into the target tissue organ.

11. A hand held and operated, re-usable biopsy gun to be used with a biopsy needle to obtain a tissue sample from a target tissue organ, said target organ being a soft tissue organ or a bone organ, said biopsy gun comprising:
   a firing mechanism for firing a biopsy needle with a minimum force for striking and penetrating said target tissue organ;

a triggering mechanism;

a disposable syringe having a plunger;

a cradle for holding said biopsy needle and said disposable syringe, wherein said disposable syringe is attached to said needle, such that on actuation of said triggering mechanism, said firing mechanism is actuated causing said cradle together with said biopsy needle and attached disposable syringe to fire forwards in a forward stroke to permit said biopsy needle to strike a target tissue organ, causing a first tissue sample to be cored off into said needle and said syringe to obtain a second tissue sample using a vacuum created when said plunger is maintained in a rearward position while said syringe is fired forward.

12. A hand held and operated, re-usable biopsy gun according to claim 11, wherein said target tissue organ is a target bone organ, said first tissue sample is a cored bone tissue, and said second tissue sample is a liquid bone marrow sample.

13. A hand held and operated, re-usable biopsy gun according 11, which is powered by a rechargeable battery.

* * * * *